(12) United States Patent
Dafforn et al.

(10) Patent No.: US 10,329,599 B2
(45) Date of Patent: Jun. 25, 2019

(54) MOLECULAR DETECTION SYSTEM

(71) Applicant: The University of Birmingham, Birmingham (GB)

(72) Inventors: Timothy Dafforn, Warwickshire (GB); Matthew Hicks, West Midlands (GB)

(73) Assignee: The University of Birmingham, Birmingham (GB)

( * ) Notice: Subject to any disclaimer, the term of this patent is extended or adjusted under 35 U.S.C. 154(b) by 127 days.

(21) Appl. No.: 15/314,027

(22) PCT Filed: May 28, 2015

(86) PCT No.: PCT/GB2015/051545
§ 371 (c)(1),
(2) Date: Nov. 25, 2016

(87) PCT Pub. No.: WO2015/181547
PCT Pub. Date: Dec. 3, 2015

(65) Prior Publication Data
US 2017/0198338 A1    Jul. 13, 2017

(30) Foreign Application Priority Data

May 28, 2014  (GB) .................................. 1409427.0

(51) Int. Cl.
| | | |
|---|---|---|
| *C12Q 1/68* | (2018.01) | |
| *G01N 21/77* | (2006.01) | |
| *C12Q 1/6825* | (2018.01) | |
| *C12Q 1/6816* | (2018.01) | |
| *C12Q 1/6844* | (2018.01) | |

(52) U.S. Cl.
CPC ......... *C12Q 1/6825* (2013.01); *C12Q 1/6816* (2013.01); *C12Q 1/6844* (2013.01); *G01N 21/77* (2013.01); *G01N 2021/7769* (2013.01)

(58) Field of Classification Search
CPC ...................... C12Q 1/6825; G01N 2021/7769
See application file for complete search history.

(56) References Cited

U.S. PATENT DOCUMENTS

| | | | |
|---|---|---|---|
| 2009/0203000 A1* | 8/2009 | Mutharasan | G01N 33/54373 435/6.12 |
| 2010/0053619 A1* | 3/2010 | Dafforn | G01N 21/19 356/436 |

FOREIGN PATENT DOCUMENTS

| | | |
|---|---|---|
| WO | WO2000/040751 A2 | 7/2000 |
| WO | WO2002/079755 A2 | 10/2002 |
| WO | WO2003/026590 A2 | 4/2003 |
| WO | WO2008/059280 A1 | 5/2008 |

\* cited by examiner

*Primary Examiner* — David C Thomas
(74) *Attorney, Agent, or Firm* — Brooks Kushman P.C.

(57) ABSTRACT

A molecular sensor that utilizes dichroism can be used to identify the presence of a target nucleic acid molecule in a sample, for example during or after amplification reactions such as PCR/thermocyling reactions and isothermal reactions. A sensor element for use in the molecular sensor may comprise an alignable scaffold/receptor complex, the receptor of said complex comprising a nucleic acid sequence which is complementary to at least a portion of a target nucleic acid molecule.

10 Claims, 3 Drawing Sheets

MOLECULAR DETECTION SYSTEM

FIELD OF THE INVENTION

The present invention relates to a molecular sensor that utilises dichroism to identify the presence of a nucleic acid molecule in a sample, particularly but not exclusively during or after an amplification reaction including but not limited to PCR/thermocyling reactions and isothermal reactions. The invention also relates to a sensor element for use in the sensor.

BACKGROUND TO THE INVENTION

By their nature, organisms contain many complex molecules and molecular assemblies. Some of the most important molecules and assemblies, including DNA, have high aspect ratios (i.e. one axis significantly greater in length than any other). It is known to use an optical apparatus to specifically detect these high aspect ratio molecules. Such an apparatus relies on the way these long molecules interact with polarised light (i.e. light with an electric field established in one direction only).

The phenomenon being exploited in the above apparatus is known as dichroism. The incident light may be either linearly polarised, giving rise to linear dichroism (LD), or circularly polarised, giving rise to circular dichroism (CD). LD is the property exhibited by some molecular structures whereby linearly polarised light is differentially absorbed along two orthogonal axes. CD relates to the difference in absorption of left and right circularly polarised light. A molecule that is capable of selective light absorption is known as a chromophore. Dichroic molecules, i.e. those that exhibit dichroic properties, are a particular type of chromophore. Examples of dichroic materials are certain natural crystals, stretched polymers, and other non-isotropic molecules. Biomolecules contain a wide range of chromophores (including aromatic side chains, nucleotides and peptide backbones).

In order to be able to observe a dichroic effect, it is necessary that the chromophores be aligned, or at least partially aligned, with respect to the incident polarised light beams. Some examples of moieties of interest that have been successfully aligned include linear biomolecules in the form of DNA, fibrous proteins and membranes (including membrane proteins) (Marrington R, Small E, Rodger A, Dafforn T R, Addinall S G, "FtsZ fiber bundling is triggered by a conformational change in bound GTP" J Biol Chem 2004; 279(47):48821-48829; Dafforn T R, Rajendra J, Halsall D J, Serpell L C, Rodger A, "Protein fiber linear dichroism for structure determination and kinetics in a low-volume, low-wavelength couvette flow cell" Biophys J 2004; 86(1 Pt 1):404-410; Dafforn T R, Rodger A, "Linear dichroism of biomolecules: which way is up?" Curr Opin Struct Biol 2004; 14(5):541-546; Halsall D J, Rodger A, Dafforn T R, "Linear dichroism for the detection of single base pair mutations" Chem Commun (Camb) 2001(23):2410-2411).

A particularly convenient method for aligning such molecules is to create a solution including the molecules and then to flow the solution. Due to the elongate nature of the molecules, alignment arises as a result of shear forces generated by the flow, making the sample suitable for exhibiting the effect of linear dichroism.

In a known apparatus, once the molecules of interest have been aligned, linearly polarised light is directed through the solution from a direction substantially perpendicular to the axes of the aligned molecules. Absorption of light occurs within a molecule because, at a particular wavelength, the electric field of radiation urges the electrons in the molecule in a particular direction. When several molecules are similarly aligned, the electrons in each are all characterised by the same preferred net displacement direction. LD is a measure of the difference of absorbance of the incident light between two orthogonal polarisations. Varying the wavelength of the incident light and detecting the light emerging from the sample, allows a spectrum to be obtained which illustrates the absorbance of the sample with respect to wavelength.

An LD spectrum of a molecule provides information on the chromophores that are present including the orientation of the chromophores (and hence molecular conformation) and the orientation of the chromophores with respect to the axes of polarization. This information is important in understanding the structure of the molecule. Note that LD is a measurement of a sample's bulk property. The strength of the absorbance can be used to quantify the number of target molecules that are present in the sample. In addition, since LD is extremely sensitive to changes in alignment, an anomaly in the structure of a molecule may be detected. For example, LD can detect the distortion caused by a single mismatched hydrogen bond in a 1300 bp (base pair) fragment of DNA.

Furthermore, LD is extremely sensitive to the formation of a complex since the binding of an aligned molecule to a second molecule has the following two measurable effects:
1) The shape of the aligning moiety is altered and this results in its alignment also being altered, which leads to a change in the observed LD spectrum.
2) The second molecule itself becomes aligned by virtue of its attachment to the aligned molecule. This leads to the generation of an LD signal for the previously unaligned chromophores of the second molecule. Thus, information on the structure of the complex can be obtained.

Both of the above effects result in detectable phenomena that can be used to detect the formation of complexes. Not only can structural information be gleamed regarding the nature of the complex but the affinity of the interaction can also be determined.

There are many areas in which it is desirable to detect the presence of a specific of nucleic acid sequence. For example, in the detection of disease or bio-markers for particular genes the nucleic acid sequence can be used to detect the presence of a pathogen or a gene. In addition, the amount of the specific sequence that is present can be quantified.

One example of a method to detect small amounts of DNA is the polymerase chain reaction (PCR) in which DNA is amplified by a replication process using an enzyme and suitable substrates. The original double stranded sequence (target), if present, is separated into two single strands by the use of heat. Each single stranded DNA is bound by a short (typically 10-30 base) oligonucleotide (primer). The DNA is replicated by a (heat-stable) DNA polymerase enzyme using the target to determine the sequence and the primer as a starting point to give a new DNA molecule (amplimer). This process is repeated through several cycles to give exponential growth of the amplimer concentration. The building blocks are nucleotides.

The detection of the amplimer has previously been carried out in different ways, the main methods being:
Detection only at the end of the PCR:
1) Electrophoretic separation of the reaction components at the end of the reaction to detect the presence or absence of the nucleic acid target sequence In order to detect the increasing amounts of the product during the reaction (q-PCR) and possibly use this to infer the starting concentration of the target:

2) Use of a dye that binds to only double-stranded nucleic acids but not to single stranded
3) Use of a dye that changes its fluorescence when bound to double-stranded nucleic acid
4) Labelling the oligonucleotide primers that are used in the amplification such that there are two dye molecules on opposite ends of the oligonucleotide that quench a fluorescence signal in the free form but give a large signal when bound to their complementary sequence.

As mentioned above, it is possible to detect DNA directly from its LD signal. In this approach the amplimer is detected directly, without the use of dyes, by virtue of its ability to align in shear flow in solution to a greater extent than the primers or nucleotides. The alignment is induced either by flow through a thin tube (capillary) or by Couette flow. The latter is achieved by the use of two coaxial cylinders (one inside the other) with an annular gap between them. One cylinder is rotated relative to the other and a shear gradient is formed causing some molecules that have one axis much longer than the other to align. In samples where there is a lot of amplimer the difference in absorbance will be large giving a large LD signal. In addition to being able to detect the amplimer at different cycle numbers, recently, through technical advances in the speed of heating and cooling the LD cells, it has become possible to carry out the amplification reaction in the LD alignment cell and to perform q-PCR. However, this approach of detecting the amplimer directly has two large disadvantages:

1) The amplimer must be long (>around 400 base pairs)
2) There is no scope for multiplexing (see below)

WO 2008/059280 discloses a molecular sensor in which the sensor element comprised a scaffold moiety with a high aspect ratio having a receptor moiety attached thereto. The use of an alignable scaffold moiety as a substrate for the attachment of a receptor moiety meant that neither the receptor moiety itself nor the target molecule required inherent alignment properties. As well as being able to identify the aligned molecules through the resulting dichroic spectrum, the sensor can be used to quantify the aligned molecules and to detect the presence of molecular anomalies such as mismatches. The binding properties of the receptor moiety and target molecule may also be studied using the sensor. The inherent nature of dichroic molecules means that the sensor is extremely sensitive.

The present invention represents a further development of the sensor disclosed in WO 2008/059280 and aims to improve the application of dichroic analysis to nucleic acid molecules.

SUMMARY OF THE INVENTION

According to a first aspect of the present invention there is provided a method of detecting a target nucleic acid molecule in a sample, said method comprising;
providing an alignable scaffold/receptor complex, the receptor of said complex comprising a nucleic acid sequence which is complementary to at least a portion of the target nucleic acid molecule,
exposing the scaffold/receptor complex to the sample whereby to bind the receptor to the target nucleic acid molecule if present
inducing alignment of the scaffold/receptor/target complex
using LD to detect a change in the alignment of the scaffold/receptor complex effected by binding of the target nucleic acid molecule, if present, to the receptor.

The target nucleic acid molecule may be single-stranded or double-stranded where in the case of the latter, the double-stranded nucleic acid molecule is either i) partially denatured to allow binding of the receptor to the complementary strand or ii) there is formation of a triple-stranded complex where the receptor binds to the double-stranded target.

The change in alignment of the scaffold/receptor complex caused by binding of the target molecule may be a decrease in alignment or an increase in alignment. The former is effected by disruption of alignment due to i) the cross-linking of scaffold/receptor complexes by the target or ii) a change in the hydrodynamic properties in the scaffold/receptor/target complex that results in a lower alignment. The latter is effected by a change in the hydrodynamic properties in the scaffold/receptor/target complex that results in a higher alignment for example via the association of a very long target molecule with the scaffold/receptor.

Alignment of the scaffold/receptor complex may be achieved by any method known to those skilled in the art. For example, the scaffold/receptor complex may be aligned by shear flow, magnetic alignment, electrophoretic effects or by using squeezed gels. Methods for detecting the LD signal of the scaffold/receptor complex will be known to those skilled in the art.

In some embodiments, the method comprises providing at least a first and a second alignable scaffold/receptor complex. In an embodiment, the first and second scaffold/receptor complexes bind to different target nucleic acids. In this embodiment, the receptor of the first complex comprises a nucleic acid sequence that is different to that of the receptor of the second complex. In a particular embodiment a plurality of distinct types of scaffold/receptor complexes is used, wherein the receptors in each type of complex comprise a different nucleic acid sequence for binding different target nucleic acids. This embodiment permits multiplexing, i.e. the detection of multiple different target nucleic acids in a single assay. This requires different chromophores to be attached to the scaffold/receptor complexes such that a different LD signal is detected for each target.

In another embodiment, a first and a second scaffold/receptor complex is provided, each of which binds to the same target nucleic acid. In this embodiment, the receptor of the first complex comprises a nucleic acid sequence which is complementary to a first portion of the target nucleic acid, and the receptor of the second complex comprises a nucleic acid sequence which is complementary to a second portion of the target nucleic acid.

In a further embodiment wherein the target nucleic acid is double-stranded, the receptor of the first complex comprises a nucleic acid sequence which is complementary to at least a portion of one strand of the double-stranded target nucleic acid molecule, and the receptor of the second complex comprises a nucleic acid sequence which is complementary to at least a portion of the other strand of the double-stranded target nucleic acid molecule. A double-stranded target nucleic acid molecule may simultaneously bind to a receptor on a first complex and to a receptor on second complex, thereby causing cross-linking between the first and second complexes, resulting in a decrease in the alignment of the complexes which is detectable by LD.

The method may further comprise a step of amplifying the target nucleic acid molecule which may be present in the sample. This is particularly useful where the concentration of the target nucleic acid molecule in the sample is low. The target nucleic acid molecule may be amplified using any known amplification method which are known to those skilled in the art including, but not limited to, thermocycling methods (e.g. PCR) and isothermal methods (e.g. LAMP—loop mediated isothermal amplification or RPA—recombinase polymerase amplification). Thus, in an embodiment, the target nucleic acid molecule is an amplimer. The primers for amplification are designed such that they do not interfere with the scaffold/receptor complexes. The amplification of the target nucleic acid molecule may be carried out prior to exposure of the scaffold/receptor complex to the sample. Alternatively, the amplification step may be carried out in the presence of the scaffold/receptor complex. In this embodiment, the amplification reaction is carried out in an LD alignment cell. Changes in the alignment of the scaffold/receptor complex, caused by the binding of amplimers to the scaffold/receptor complex, can then be monitored during the amplification reaction.

The receptor may comprise an oligonucleotide, such as a DNA or an RNA molecule, or the receptor may comprise a PNA (peptide nucleic acid) molecule or aptamers.

In an embodiment, the receptor consists of a nucleic acid sequence which is complementary to at least a portion of the target nucleic acid molecule. In a particular embodiment, the receptor consists of an oligonucleotide or other molecule that exhibits sufficient specificity for the target.

The receptor nucleic acid or other molecule needs to have sufficient specificity for the target such that it will distinguish it from other non-target molecules. This does not mean that the sequence of, for example, the nucleic acid must have complete complimentarity to the target. The amount of complimentarity to the target that comprises sufficient specificity for the application will depend on the temperature, ionic strength and other physico-chemical parameters.

It will be understood that the binding strength of nucleic acid sequences to one another is a well-known parameter that can be calculated based on the sequence. If there is natural variation in the target sequence then it is possible to produce a multitude of receptor sequences that have some of the sequence randomized (having any of the bases at one or more sites in the sequence).

As used herein a high aspect ratio relates to an aspect ratio greater than 5:1, greater than 10:1, greater than 20:1, greater than 50:1, greater than 75:1 and in some embodiments greater than 100:1.

The scaffold moiety may have a high aspect ratio or the scaffold/receptor complex may have a high aspect ratio.

Examples of suitable scaffold moieties include
synthetic polymers,
carbon nanotubes,
biomolecular fibres
crystals
inorganic particles, e.g. metal fragments
synthetic biology constructs
mixtures of liquids of different polarities (so as to create phase separation and subsequent alignment of regions of the minor phase)

As used herein a biomolecular fibre is any biomolecule having the required high aspect ratio and which is alignable under flow conditions. Examples of biomolecular fibres include lipid vesicles, filamentous bacteriophage and polymers such as amino acid polymers (i.e. polypeptides or proteins) and nucleic acid polymers (i.e. RNA or DNA).

In certain embodiments the biomolecular fibre is a filamentous bacteriophage, such as M13, f1, fd, Ike and N1.

In some embodiments the scaffold may be modified by the addition of a chromophore, such that the scaffold itself need not be inherently dichroic. The chromophore is attached to the scaffold moiety in such a way that it is not in free exchange with the other scaffold moieties. In certain embodiments the attachment is by one or more covalent bonds.

Examples of suitable chromophores include those in Table 1 below.

TABLE 1

| Class of Chromophore | Examples (non-exhaustive list) |
|---|---|
| AlexaFluor(AF) | AF405, AF488, AF555, AF610, AF647, AF700. |
| Spiro compounds | Fluorescamine, |
| Xanthones | e.g. Fluoresceins (Fluorescein-isothiocyanate, N-hydroxysuccinimide-Fluorescein Rhodamines (Rhodamine-isothiocyanate, Tetra-methyl-rhodamine-isothiocyanate) |
| Benzopyrones | Coumarin |
| DNA intercalators | Ethidium bromide |

According to a second aspect of the present invention there is provided a sensor element comprising an alignable scaffold/receptor complex, the receptor of said complex comprising a nucleic acid sequence which is complementary to at least a portion of a target nucleic acid molecule.

According to a third aspect of the present invention there is provided a molecular sensor for detecting a target nucleic acid molecule in a sample, the molecular sensor comprising:
  a flow path configured for flowing a solution potentially containing a target nucleic acid molecule;
  a source of polarised light;
  a detector arranged to receive light from the source after it has passed through the flow path and capable of measuring the degree of polarisation of the light in two orthogonally orientated polarisations; and
  a sensor element according to the second aspect of the present invention.

It will be understood that the light source itself may produce polarised light or a suitable filter may be applied between the light source and the flowpath. Alternatively the sensor may use unpolarised light with detection of the polarisation of the light being entirely within the detector.

The flowpath may be conveniently provided by a Couette cell or a simple flow channel for example in a plastic chip.

BRIEF DESCRIPTION OF THE DRAWINGS

The invention will be further described by way of example only with reference to the accompanying drawings in which.

DETAILED DESCRIPTION OF CERTAIN EMBODIMENTS

Figure 1:
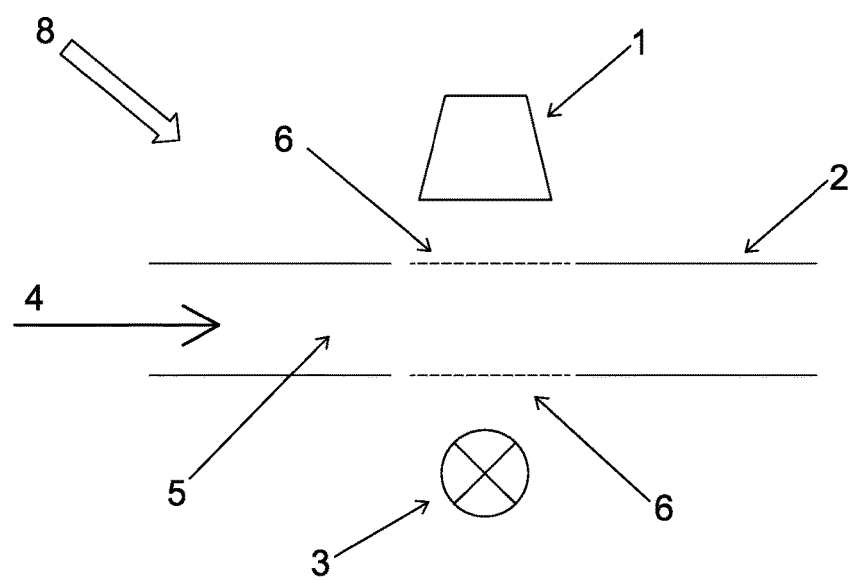
FIG. 1 is a schematic of a sensor in accordance with an embodiment of the present invention.

With reference to FIG. 1, there is illustrated a molecular sensor 8 according to the present invention. The sensor 8 comprises a flow path in the form of an elongate pipe 2 that is mostly made from plastic and is opaque. The central portion of the pipe 12 is configured as an observation window 6 and is made from a material that is transparent to the wavelength of light employed. In this particular example, the observation window 6 is made from glass quartz, which is transparent to visible light. Thus, in this example the observation window 6 is configured to allow light in the wavelength range of approximately 400 nm to 700 nm to pass therethrough. Adjacent one side of the observation window 6 is a light source 3. The light source 3 is configured to emit two orthogonal linearly polarised beams of light through the observation window 6 and thereby through the flow path 5. Disposed opposite to the light source 3, on the other side of the observation window 6 and the flow path 5, is a detector 1. The detector 1 is configured to detect the light beams emitted by the light source 3 once they have passed through the observation window 6 and the flow path 5.

In use, a liquid solution containing a plurality of sensor elements each comprising (i) an alignable scaffold moiety (and bound chromophore) having a high aspect ratio and (ii) one or more receptors comprising a nucleic acid sequence which is complementary to at least a portion of a target nucleic acid molecule is exposed to a sample to be analysed. The sample, which may include the target nucleic acid of interest, is flowed through the pipe 2 in the direction indicated by arrow 4 in FIG. 1.

Figure 2A:
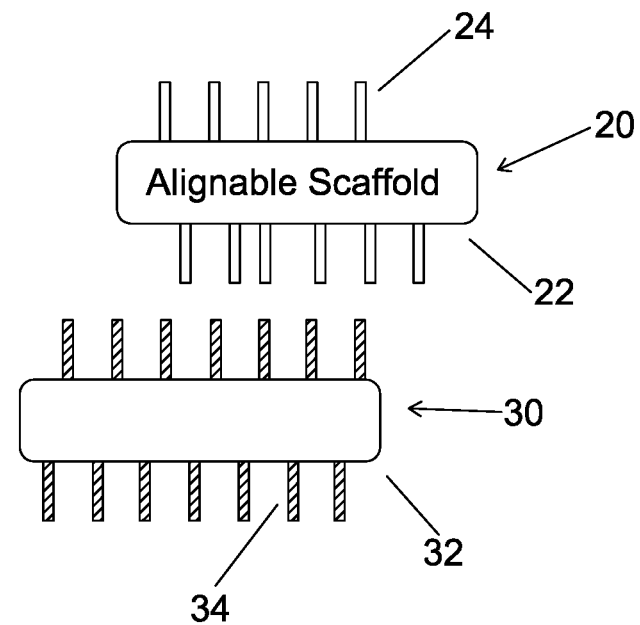
FIG. 2a is a schematic of first and a second scaffold/receptor complexes in accordance with an embodiment the present invention, prior to exposure to a sample containing a target nucleic acid.

Referring to FIG. 2a, a first alignable scaffold/receptor complex 20 comprises a scaffold moiety 22 to which is attached a plurality of receptors 24, each receptor comprising a sequence which is complementary to a portion of a target nucleic acid molecule (not shown). In the embodiment shown, a second scaffold/receptor complex 30 is provided comprising a scaffold moiety 32 having attached thereto a plurality of receptors 34. The receptors 34 comprise a sequence which is also complementary to a portion of the target nucleic acid molecule, but which is different to the sequence of the receptors 24 on the first scaffold/receptor complex 20.

Figure 2B:
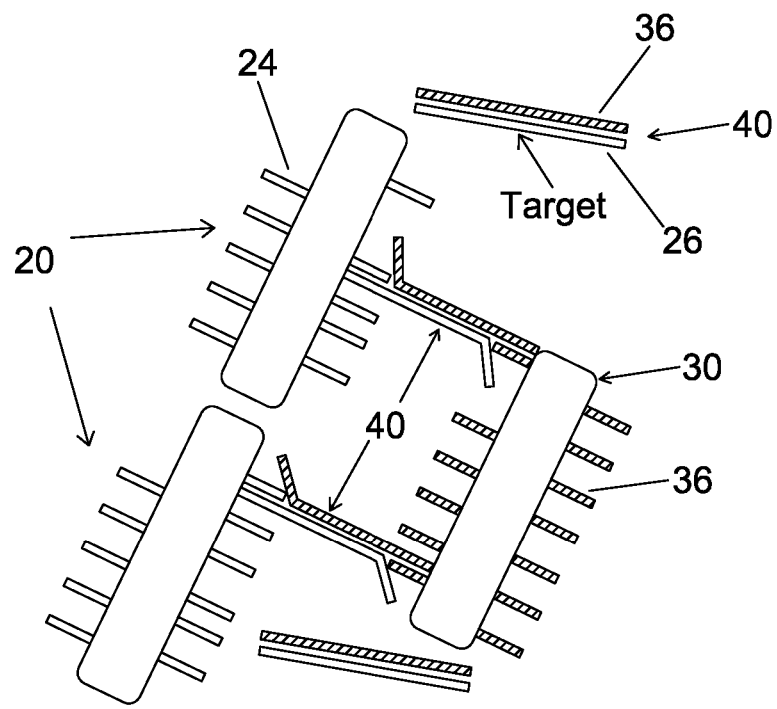
FIG. 2b is a schematic of first and second scaffold/receptor complexes binding to a target nucleic acid, in accordance with an embodiment of the present invention

As shown in FIG. 2b, the sequence of the receptors 24 is complementary to a portion of one strand 26 of a double-stranded target nucleic acid molecule 40, while the sequence of the receptors 34 is complementary to a portion of the opposite strand 36 of the target nucleic acid molecule 40. When the scaffold/receptor complexes 20, 30 are exposed to a sample containing the target nucleic acid molecules 40, the receptors 24, 34 hybridise with the strands of the target nucleic acid molecules 40 by virtue of the complementary sequences. As shown in FIG. 2b, a single target nucleic acid molecule 40 may hybridise with a receptor 24 on a first scaffold/receptor complex 20 and with a receptor 34 on a second scaffold/receptor complex 30, thereby causing the complexes 20, 30 to be cross-linked together. This cross-linking of the complexes 20, 30 changes the alignment of the scaffold/receptor complexes 20, 30 in solution. The change in alignment is detected by LD.

Figure 3:
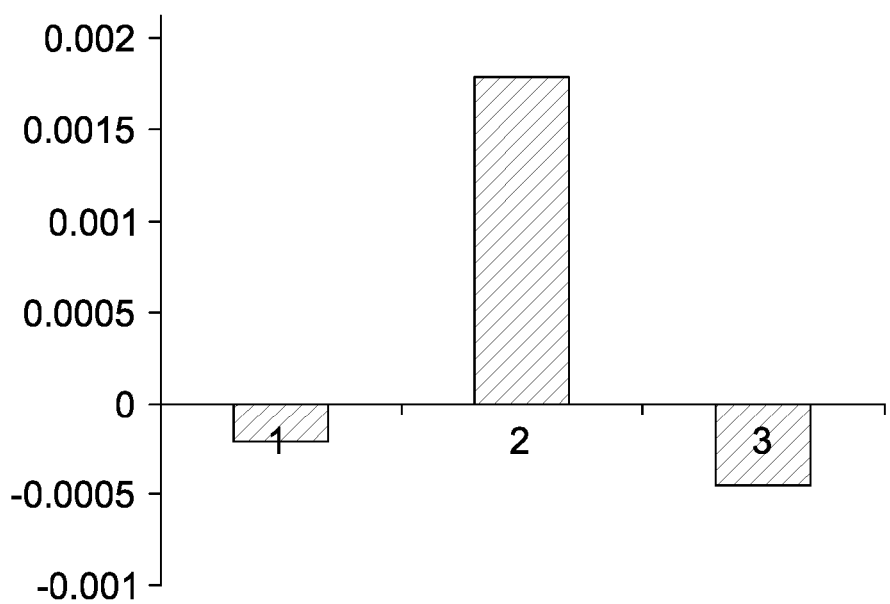
FIG. 3 is an example of LD signals at 220 nm in the absence and presence of the target molecule with appropriate controls.

This can be done for example to detect the presence of a gene for example the ampicillin resistance gene in *E. coli*. Referring to FIG. 3, the LD signal in this case is from the inherent LD signal from the scaffold molecule chromophores but could also be carried out using other chromophores that are conjugated to the scaffold molecule. Sample 1 is a PCR carried out with forward and reverse primers to an ampicillin resistance gene on a bacterial plasmid but with no scaffold molecule present, so minimal LD signal is expected. Sample 2 is a PCR carried out with the forward primer conjugated to the scaffold molecule to form a scaffold/receptor complex and a reverse primer that is not conjugated to a scaffold molecule. This has been carried out in the absence of the target ampicillin resistance gene. This sample represents a negative sample in the assay. Sample 3 is a PCR carried out with the forward primer conjugated to the scaffold molecule to form a scaffold/receptor complex and a reverse primer that is not conjugated to a scaffold molecule. This has been carried out in the presence of the target ampicillin resistance gene. This sample represents a positive sample in the assay. The sample in 1 shows that the PCR product does not interfere significantly with the assay. The reduction in signal between samples 2 and 3 shows that the target DNA containing the ampicillin resistance gene can be detected using this assay.

The invention claimed is:

1. A method of detecting a target nucleic acid molecule in a sample, said method comprising;
    providing an alignable scaffold/receptor complex, the receptor of said complex comprising a nucleic acid sequence which is complementary to at least a portion of the target nucleic acid molecule,
    exposing the scaffold/receptor complex to the sample whereby to bind the receptor to the target nucleic acid molecule if present,
    inducing alignment of the scaffold/receptor/target complex, and
    using linear dichroism (LD) to detect a change in the alignment of the scaffold/receptor complex effected by binding of the target nucleic acid molecule, if present, to the receptor,
    wherein at least a first and a second alignable scaffold/receptor complex are provided and
    wherein each of the first and second scaffold/receptor complex binds to the same target nucleic acid, the receptor of the first complex comprising a nucleic acid sequence which is complementary to a first portion of the target nucleic acid, and the receptor of the second complex comprising a nucleic acid sequence which is complementary to a second portion of the target nucleic acid.

2. The method according to claim 1, wherein alignment of the scaffold/receptor complex is achieved by shear flow, magnetic alignment, electrophoretic effects or by using squeezed gels.

3. The method according to claim 1 wherein the target nucleic acid is double-stranded, the receptor of the first complex comprises a nucleic acid sequence which is complementary to at least a portion of one strand of the double-stranded target nucleic acid molecule, and the receptor of the second complex comprises a nucleic acid sequence which is complementary to at least a portion of the other strand of the double-stranded target nucleic acid molecule.

4. The method according to claim 1 further comprising a step of amplifying the target nucleic acid molecule which may be present in the sample.

5. The method according to claim 4 wherein the amplification step is carried out in the presence of the scaffold/receptor complex.

6. The method according to claim 1 wherein the receptor comprises an oligonucleotide, a peptide nucleic acid molecule or an aptamer.

7. The method according to claim 1 wherein the scaffold moiety or the scaffold/receptor complex has a high aspect ratio.

8. The method according to claim 1 wherein the scaffold moiety is selected from the group consisting of synthetic polymers, carbon nanotubes, biomolecular fibres, crystals, inorganic particles, synthetic biology constructs and mixtures of liquids of different polarities.

9. The method according to claim 8 wherein the biomolecular fibre is a filamentous bacteriophage, such as M13, f1, fd, Ike and N1.

10. The method according to claim 1 wherein the scaffold is modified by the addition of a chromophore.

* * * * *